United States Patent [19]

Hatch

[11] Patent Number: 4,838,257
[45] Date of Patent: Jun. 13, 1989

[54] VENTILATOR

[76] Inventor: Guy M. Hatch, 550 E. 1400 North, Suite Q, Logan, Utah 84321

[21] Appl. No.: 74,730

[22] Filed: Jul. 17, 1987

[51] Int. Cl.[4] ............................................ A61M 16/00
[52] U.S. Cl. ........................... 128/204.18; 128/204.19; 128/204.21; 128/205.24
[58] Field of Search ................... 128/204.18, 204.19, 128/204.21, 205.24, 204.22, 202.23

[56] References Cited

U.S. PATENT DOCUMENTS

| 2,918,917 | 12/1959 | Emerson | 128/205.24 |
|---|---|---|---|
| 3,863,082 | 1/1975 | Gillot et al. | 128/205.18 |
| 3,903,881 | 9/1975 | Weigl | 128/204.25 |
| 4,036,221 | 7/1977 | Hillsman et al. | 128/204.23 |
| 4,141,356 | 2/1979 | Smargiassi | 128/204.23 |
| 4,197,843 | 4/1980 | Bird | 128/204.25 |
| 4,204,536 | 5/1980 | Albarda | 128/204.22 |
| 4,336,590 | 6/1982 | Jacq et al. | 128/204.22 |
| 4,344,144 | 8/1982 | Damico et al. | 128/204.22 |
| 4,351,329 | 9/1982 | Ellestad et al. | 128/204.21 |
| 4,393,869 | 7/1983 | Boyarsky et al. | 128/204.18 |
| 4,444,201 | 4/1984 | Itoh | 128/204.23 |
| 4,450,838 | 5/1984 | Miodownik | 128/204.23 |
| 4,459,982 | 7/1984 | Fry | 128/204.23 |
| 4,481,944 | 11/1984 | Bunnell | 128/204.18 |
| 4,527,557 | 7/1985 | DeVries et al. | 128/205.24 |
| 4,538,604 | 9/1985 | Usry et al. | 128/204.23 |
| 4,592,349 | 6/1986 | Bird | 128/205.24 |

FOREIGN PATENT DOCUMENTS 140487 5/1985 European Pat. Off. .
2063686 6/1981 United Kingdom .

OTHER PUBLICATIONS

M. R. Crawford, "High-Frequency Ventilation," Anaesthesia and Intensive Care, vol. 14, No. 3, Aug. 1986.
W. I. Marsh, M. S., "A Flexible System for Closed-Loop Ventilator Development," 12/81.
A. Nouh, "A Proposed Controlled Ventilator by Digital Computer," 1/80.
"The Way Things Work", vol. 2, Simon and Schuster, 12/1971.
The Illustrated Science and Invention Encyclopedia, "How It Works", H. S. Stuttman Co., Inc.
J. Bert Bunnell, ScD, "High Frequency Hardware: Implementation of the Latest Mode of Respiratory Therapy", 10/85.

Primary Examiner—Edward M. Coven
Assistant Examiner—John P. Lacyk
Attorney, Agent, or Firm—Wells, St. John & Roberts

[57] ABSTRACT

The respirator system controls operation of an exhale gas pressure control valve and an delivery gas flow control valve interposed in tubes leading to the patient's airway. Each control valve is operated by a Venturi flow pilot valve having a variable exhaust flow which is a function of an electromagnetic linear actuator. Operation of the electromagnetic actuator is accurately controlled by computer hardware and software, which can operate the pilot valves to meet a wide range of ventilation modes for patients of any size or physical condition.

18 Claims, 6 Drawing Sheets

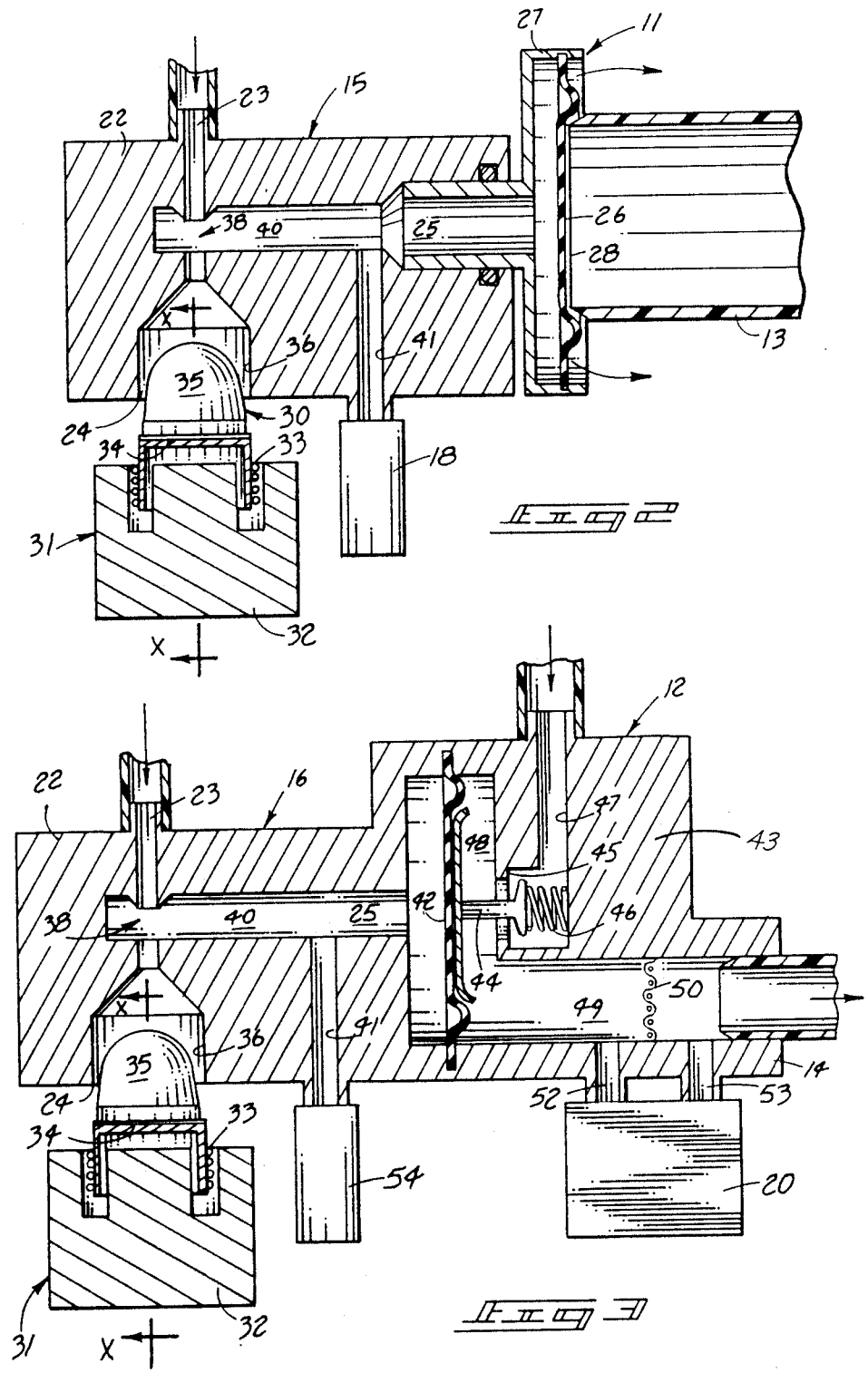

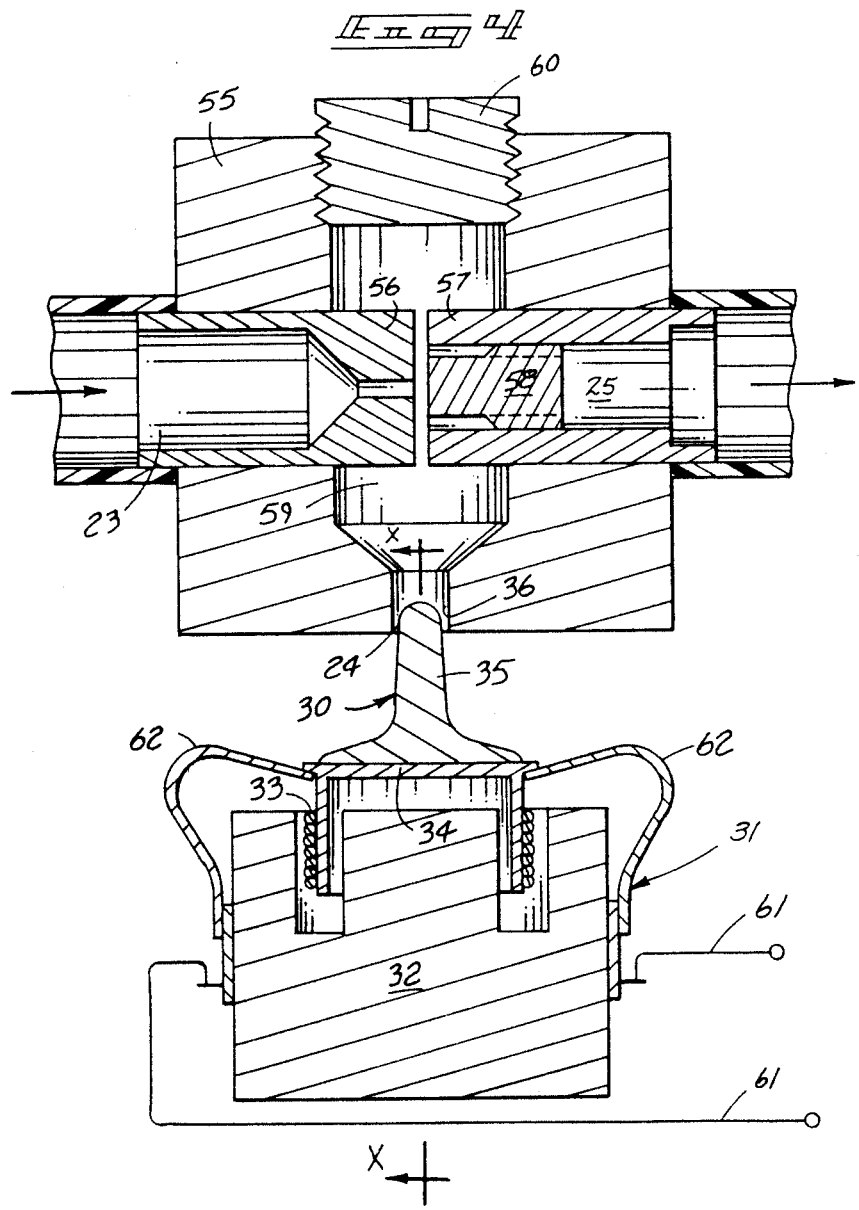

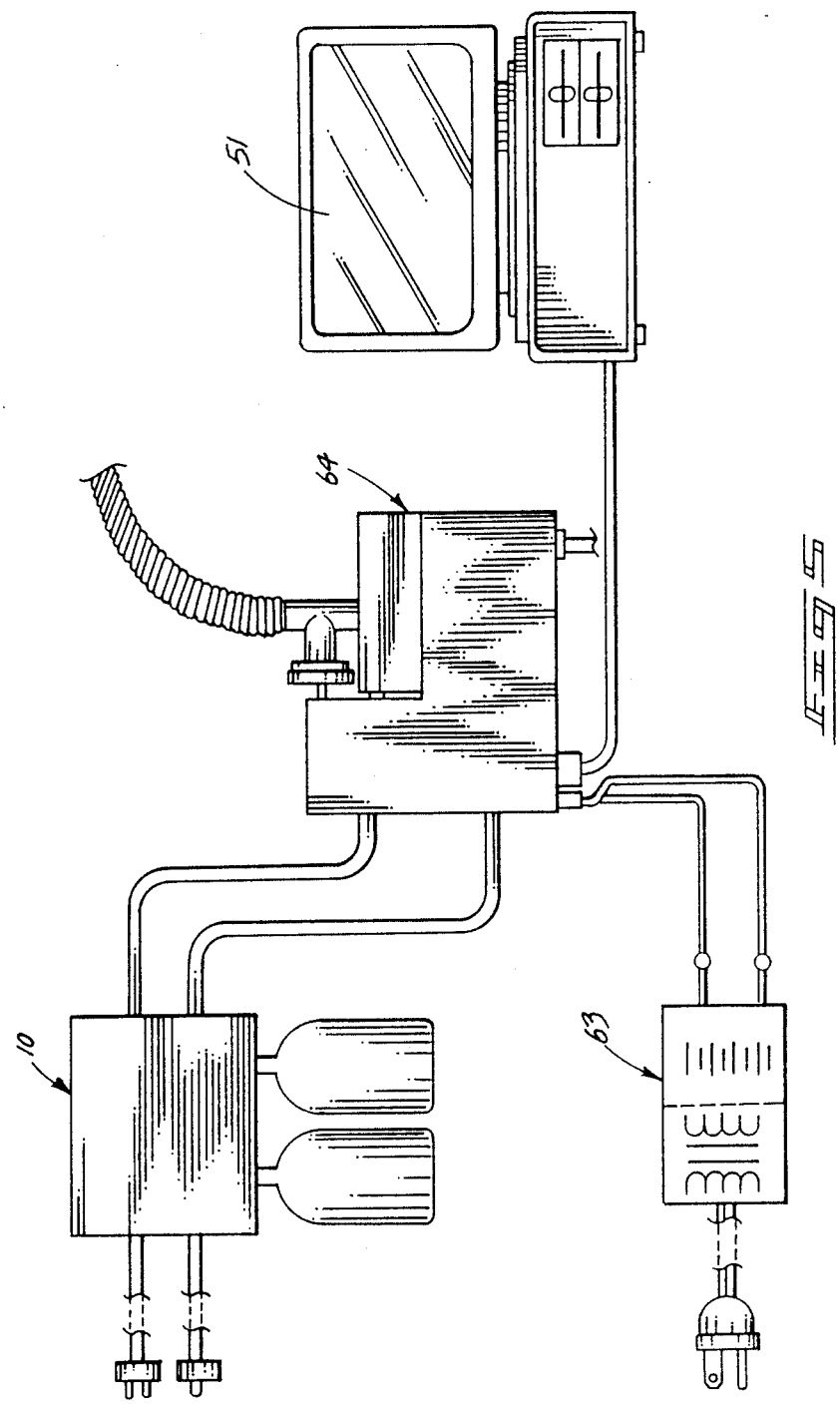

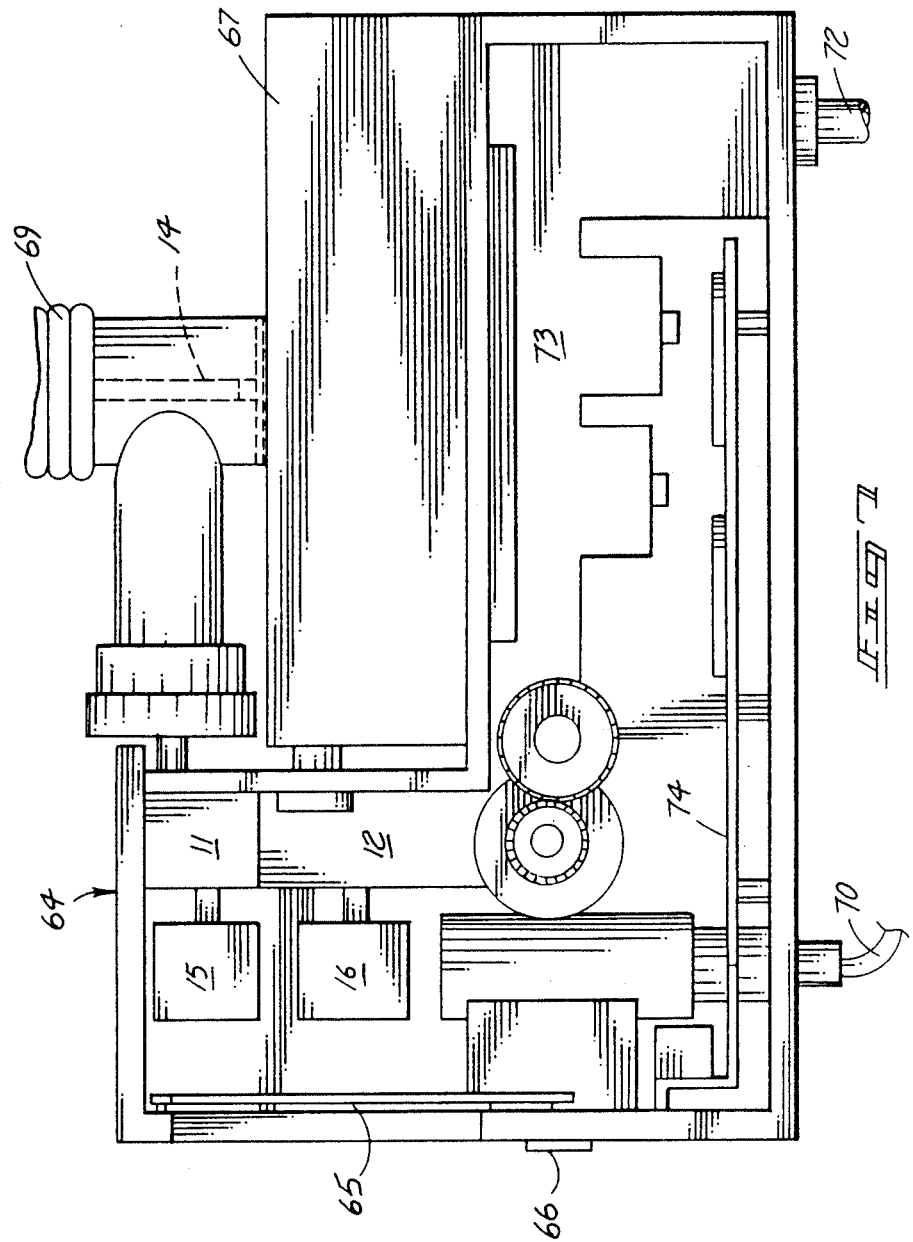

VENTILATOR

TECHNICAL FIELD

This disclosure relates to respirator systems for ventilating the lungs of a patient, where resipiratory gas is supplied to the patient under positive pressure conditions controlled by a computer.

BACKGROUND OF THE INVENTION

The present disclosure relates to the physical components by which operational control functions are implemented in a respirator to control gas flow and pressure delivered to the patient. As respirator technology has developed, great efforts have been made to enhance the limited phsyical behavior of available valves and other mechanical devices used for controlling gas flow and pressure. These enhancements have resulted in the production of ventilators of increasing mechanical and operational complexity, despite the fact that the available respirator still preform only relatively basic control functions. To accommodate the limitations of key physical components, such as valves, "specialty" respirators or ventilators which can perform only a portion of the total therapeutic range of treatment have been needed to carry out more advanced therapeutic modes, such as High Frequency Ventilation.

For a respirator to perform over the full range of needed functions for all patients of any age or condition, the control mechanisms for the gas delivery system must be capable of the most demanding mechanical tasks, namely High Frequency Ventilation (HFV) and therapy for tiny, premature infants. Mechanical reliability, functional stability in conventional settings for Continuous Positive Airway Pressure (CPAP) and Intermittent Mandatory Ventilation (IMV) and ease of manufacture are typically favored by designing larger dimension components. However, the larger mass and compression volume encountered in the use of larger components prevents them from operating effectively at higher ventilating frequencies and with smaller patients.

Using smaller dimension components to allow high frequency response increases mechanical instability. This instability, in turn, must be manageably by reliable means to allow use with the conventional therapy modes. Finally, manufaturing technology requirements should, if possible, be reduced by relying more upon electronic means for the elaborate control processing such a multi-function ventilator requires. Mechanical/pneumatic control devices should therefore be kept small in size, simple in operation, readily maintainable, and inexpensive to manufacture. Operation and stability should be primarily managed by means of computer controls. This increases functional capability of the system and reduces its manufacturing costs.

The present invention relates to a pulmonary ventilation assistance system, designed in the preferred embodiment specifically, but not limited to this application, for use with very low birth weight premature infants. The following important limitations of current respirator technology are addressed by the present invention:

(1) mechanical limitations to the prevention of undesirable pressure waves in the patient circuit, (2) limited ability to design optimal pressure and flow waveforms;

(3) less than desirable variety of modalities of therapy; and (4) limited provision for on-line measurement and recording of the mechanical properties of the patient's breathing system.

Delivery of breathing assistance to very small infants requires the ability to develop precisly-controlled gas flow delivery for relatively brief time intervals. Excessive pressure levels, and the occurrence of spikes in pressure during any part of the breathing cycle, must be prevented to limit mechanical injury to the airway tissues. Since current ventilator technology uses only two reference levels, with timed switching between them to provide the "cycling" involved with breathing assistance, a surge of pressure is typically produced in the breathing circuit with each switching from the lower-pressure reference level to the higher-pressure reference level at the exhale relief valve.

Typical respirator system use a constant flow of breathable gas into the patient circuit, with the exhale valve controlling the level of pressure achieved during cycling between low and high levels. Without precise flow-rate-vs-time control during each cycle, the operator is severely limited in the ability to provide an optimum mechanical transfer function between the machine and the patient's lungs.

The capability to produce breathing cycle frequencies, from zero (for Continuous Positive Airway Pressure) to as high as 20 Hz (for High Frequency Ventilation), is needed for optimum function. No current technology allows use of this full range in one instrument. Further, research with experimental techniques of breathing assistance, using combinations of different types of ventilation assistance devices, has shown the value of combinations of modalities. One such method superimposes a High Frequency Ventilation (HFV) waveform over simultaneous Intermittent Mandatory Ventilation (IMV) cycling. Another typical combination in such research is alternating periods of High Frequency Ventilation (HFV) and periods of either conventional Intermittent Mandatory Ventilation (IMV) or Continuous Positive Airway Pressure (CPAP). Further research will certainly reveal additional functions which may have merit with specific conditions. Again, no single instrument presently allows such combinations and complex cycling waveforms or the facility to conveniently provide newly designed ones in the future.

While several studies involving intermittent pulmonary function analysis have been reported, no ventilatory support device is available which measures such basic pulmonary function parameters as tidal volume, compliance and airway resistance in newborns continuously in the course of delivering ventilatory assistance. Research systems typically interpose gas flow sensing devices directly into the endotracheal tube attachment portion of the breathing circuit, allowing precise measurement of gas flow and airway pressure. Such a setup increases the "dead space" volume of the patient's airway and may result in significant re-breathing of expired gas. Additionally, these measuring devices are inherently awkward when mounted in this location, can be dangerous to the patient (due to the high temperature of the flow sensor), and are subject to contamination from patient secretions. While measurements thus derived have been useful in defining disease patterns in general, individual patient care has not been routinely monitored, nor therapy guided by these intermittent measurements because of the above technical difficulties and the requirement of analyzing the data by manual methods. Research indicates optimization of ventilator therapy could be greatly facilitated by such data being available automatically, at any time, on every patient. A system proposing to do this must not interfere with on-going therapy or introduce additional risks to the patient. The present invention fills this need by means made possible by the reduced patient circuit volume and by computer control and measurement of flow and pressure in that circuit.

The prior art ventilator control systems may be grouped according to the interaction between electronic, mechanical and pneumatic components with regard to producing patterns of pressure and flow. Totally pneumatic and fluidic/pneumatic systems require no electrical power for operation. Electric motor driven, adjustable linkage piston or valve systems require electrical power and pressurized gas supply but control rate of function by the operator adjusting the motor speed. Electric solenoid valve systems use electrical power to time cycle intervals and switch pneumatic lines, but leave control of pressure and gas flow waveforms to mechanical/pneumatic devices. An additional group of respirator designs utilizes industrial proportional electric/pneumatic interface valves to directly govern pressure and gas flow waveform shapes. The present systems should be classified in this latter group.

Totally fluidic and pneumatic/fluidic systems offer simplicity of supply; using only compressed oxygen and air for both breathing gas and control functions. However, even when only basic ventilator therapy functions are offered, totally pneumatic systems must become very complex to perform acceptably. An example is illustrated by the profusion of separate devices and fittings involved in the Bird Ventilator designs U.S. Pat. Nos. 4,197,843 and 4,592,349).

Additionally, since pressure and gas flow waveform generation is primarily a mechanical function, the fixed physical properties (mass of moving parts, friction, compressible volumes, fixed restrictor orifices, etc.) of the components in fluidic based systems tend to limit their adjustable range. Currently available systems designed for operational stability in CPAP and IMV modes do not have adequate adjustable range to provide High Frequency Ventilation unless an additional set of actuation components is installed.

Finally, temperature stability of gas supplies is critical to stable operation with purely pneumatic or fluidic designs. Variations in input gas temperature will change the function of timing devices and may alter air/oxygen mixture, breathing gas flow rate and pressure levels. Due to the complexity of construction, repairs and adjustments tend to be difficult to perform.

Electric motor driven piston or valve systems utilize the sinusoidal waveform generation property of reciprocating piston pumps. The sturdiness of the relatively larger-scale components lends greater stability to cycle timing and output performance. However, the fixed properties of the components restrict their operational range. Expansion to include the full range of modern therapy modes, including CPAP, IMV and HFV, require addition of many fluidic and pneumatic components. On the other hand, purely fluidic and fluidic/pneumatic systems capable of duplicating the piston's sinusoidal function, plus CPAP, IMV and HFV, would be very complex mechanically.

Electric solenoid valve systems enhance the totally pneumatic and piston systems with electrical timing control. Pneumatic flow and pressure waveform generation remain as mechanical functions, again limited in range by the physical properties of the components. However, complex timing and electronic feedback control becomes possible. Extension of function into some of the newer therapeutic modes is also relatively easier than with the piston type designs.

Far greater control complexity may be obtained in an electronically controlled system for a tiny fraction of the manufacturing cost of achieving such capability with purely pneumatic or motor-driven mechanical systems. Maintenance of electronic circuitry is far simple and less costly than for pneumatic components performing similar functions. With the addition of electronic pressure transducers, alarm responses can be added and computation and display of such data as mean airway pressure becomes feasible.

Solenoid valve operated ventilators currently provide the major share of medical therapy and are well accepted by medical therapists. Due to fixed limitations of components, these are designed to be specialized to certain ranges of patient size. The High Frequency Ventilator designs by Ellestad, et al. U.S Pat. No. 4,351,329), Miodownik U.S. Pat. No. 4,450,838) and by Bunnell, et al. U.S. Pat. No. 4,481,944 and 4,538,604) also fit in this group and are likewise specialized to produce only HFV.

However, the growing interest and successful experience with High Frequency Ventilation therapy has encountered difficulties with clinical implementation. typical HFV therapy actually requires a "full-range" ventilator setup which will provide CPAP and IMV modes as well as HFV. Such combinations must presently be jury rigged by therapists. The manufacturers of conventional CPAP/IMV ventilators and of HFV units consider themselves marketing competitors and have not yet produced acceptable means of combining their individual products with those produced by competing companies. The design of "full-range" ventilators in an active area of product research and development.

Proportional electric/pneumatic interface valves (EP transducers), manufactured for industrial process control, are proposed in recent patents as means for generating the complex pressure and flow waveforms needed for optimal ventilator control. Boyarsky, et al. U.S Pat. No. 4,393,869) utilize an electrical to pneumatic transducer to pilot control a breathing gas supply regulator. This application allows a degree of proportional feedback control of function. Unfortunately, the success of this application is limited by the fact that available industrial EP transducers operate out of range (3–15 psi) of the pressure levels needed for ventilator controls (−0.1 to 2.0 psi). Specifically, the most critical precision range for the ventilator valve control system, is between −0.1 to 0.1 psi, especially for use with tiny premature infants and HFV. Additional pneumatic devices are needed to translate the higher control pressures from the EP transducer into the ventilator operational range. This two-stage approach results in mechanical degradation of response characteristics. Generation and feedback control of High Frequency Ventilation functions would be especially difficult.

DeVries et al. U.S. Pat. No. 4,527,557) proposes an electronically adjustable Venturi pressure generator system. The output pressure is governed by a variable restrictor valve in the exhaust port of the Venturi tube.

A stepper motor, cam and cam follower are used to move the variable restrictor valve element according to electronic control signals. The preferred embodiment of this device is listed as a flow controller to systematically adjust the inspiratory flow waveform of a ventilator. In this application, the functional waveform of a gas flow regulator is pneumatically adjusted by the variable output pressure from the Venturi pressure generator.

While remarkably simpler and more capable of pressure and flow waveform control than the prior art, this valve design remains functionally limited by the physical properties of certain of its components. The frequency response needed for a full-range ventilator system is expensive and difficult, if not impossible, with available stepper motors in this application. While an appropriately designed Venturi reference pressure generator can, potentially, have the desired frequency response, the choice of stepper motor, cam and follower to adjust it is unfortunate. The mechanical inertia and friction of the motor armature, cam and follower, plus the need to step through each step from one position to another, combine to slow response. The limited number of steps in a segment of rotation of the motor also reduces resolution. Advances in stepper motor technology will undoubtedly improve function, possibly even enough to overcome some of these problems. The expense and complexity of such motors will, however, likely continue to be limiting factors.

The system described herein, while mechanically less complex than systems shown by the prior art, uinquely offers to the user a full range of operational control from Continuous Positive Airway Pressure (CPAP), through the full range of Intermittent Mandatory Ventilation (IMV), to the upper limits of High Frequency Ventilation (HFV). This is attained because the majority of system control comes from the operation of computer software. The electro-pneumatic interface of the system is an advancement over the prior art in being capable of covering this full range, including accurate high frequency response.

BRIEF DESCRIPTION OF THE DRAWINGS

The preferred embodiment of the invention is illustraed in the accompanying drawings, in which:

FIG. 2 is a schematic cross-sectional view through the pressure control valve and associated pilot valve;

FIG. 3 is a schematic cross-sectional view through the flow control valve and associated pilot valve;

FIG. 4 is a cross-sectional view through a prototype pilot valve;

FIG. 5 is a simplified system view of the respirator components;

FIG. 7 is an interior elevational view of the patient interface module components with a side wall of the module removed.

DETAILED DESCRIPTION OF THE PREFERRED EMBODIMENT

The following disclosure of the invention is submitted in compliance with the constitutional purpose of the Patent Laws "to promote the progress of science and useful arts" (Article 1, Section 8).

Figure 1:
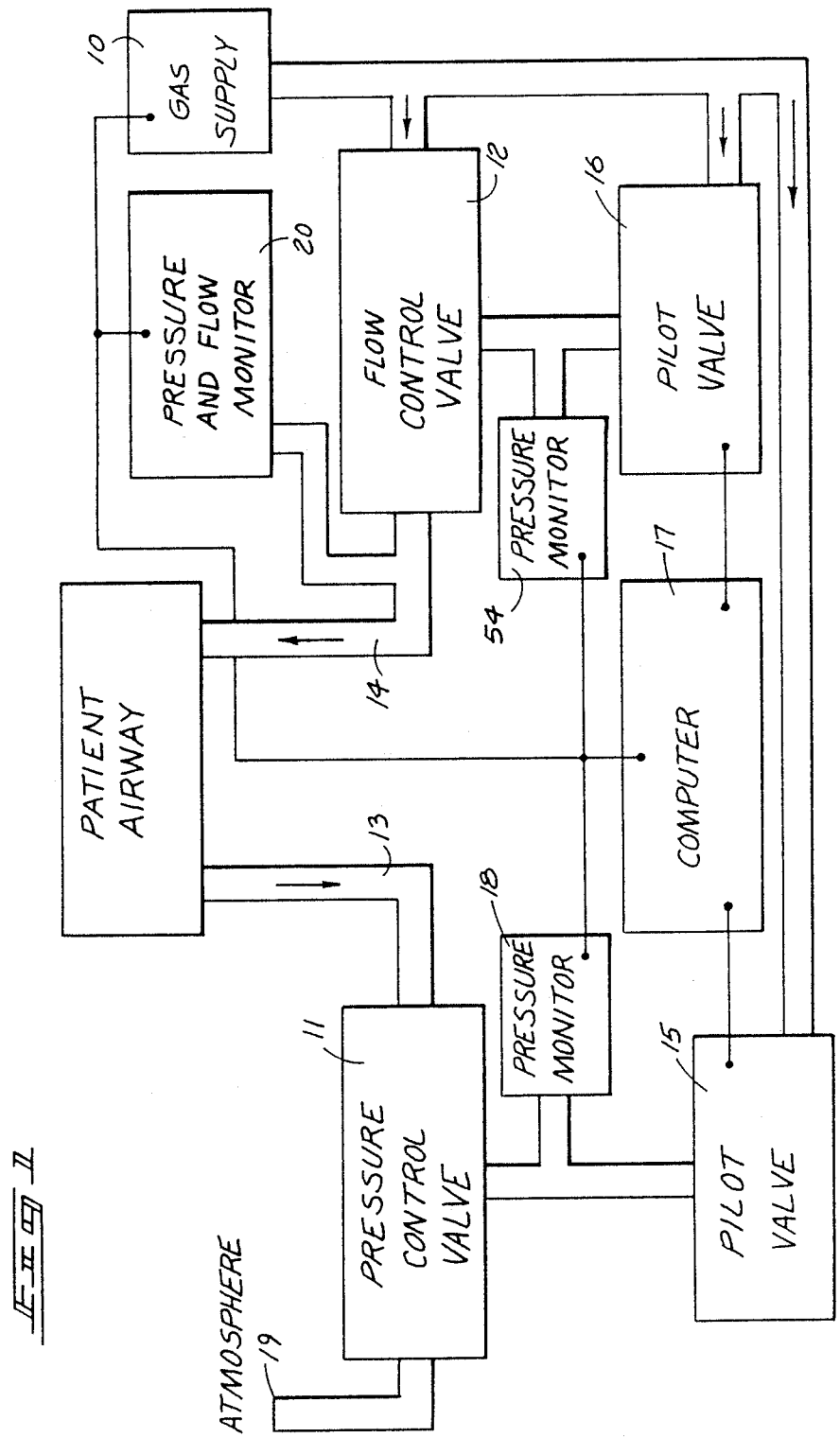
FIG. 1 is schematic block diagram of the components in the respirator system.

FIG. 1 generally describes the components of a respirator system for ventilating the lungs of a patient through the usual endotracheal tube or tracheal catheter. It includes an exhale gas pressure control valve 11 operably connected to the patient's airway through a first tube 13. It also includes a delivery gas flow control valve 12 operably connected to the patient's airway through a second tube 143. Suitably conditioned pressurized gas is directed to the flow control valve 12 from a gas supply shown generally at 10. Gas exiting from pressure control valve 11 is exhausted to atmosphere, as indicated schematically at 19. By accurately controlling instantaneous operation of valves 11 and 12, one can select the desired frequency, volume, pressure, phase relationships and waveform of gases being used to ventilate the lungs of a patient by application of this system.

Both control valves 11 and 12 are pilot-operated. The exhale gas pressure control valve 11 is controlled by operation of a Venturi pilot valve 15. The delivery gas flow control valve 12 is similarly operated by an identical Venturi pilot valve 16.

In order to maximize the responsiveness and flexibility of the respirator system, it includes a computer 17 operated according to a stored computer program and data files that determine the instantaneous operating parameters of the two pilot valves 15 and 16. The system further includes a gas pressure monitor 18 operably connected to the output of pilot valve 15, and a gas pressure monitor 54 connected to the output of pilot valve 16. A pressure and gas flow monitor 20 is operably connected to the tube 14. The monitors 18, 20 and 54 are operably connected to computer 17 in feedback loops that give the computer 17 the ability to vary operation of valves 15 and 16 to meet instantaneous needs of the patient. Further monitoring devices on the body of the patient can also be operably connected to computer 17 to measure body signs, such as temperature, heart beat, blood pressure, etc.

Referring now to FIG. 2, which schematiclaly illustrates a cross-sectional view through the essential components of the exhale gas pressure control valve 11 and pilot valve 15, the basic operational components of these elements can be described and related to one another. The control valve 11 is shown within a housing 27, while the pilot valve 15 is shown within an associated manifold 22.

Manifold 22 for the pilot valve 15 has an inlet port 23, an exhaust port 24, and a Venturi port 25. The inlet and exhaust ports 23, 24 of the pilot valve 15 lead across a region of gaseous flow 38 within the manifold 22 which is intersected perpendicularly by an opening 40 leading to the Venturi port 25. The Venturi port 25 of the pilot valve 15 in turn is operably connected to a movable diaphragm 26 arranged across an opening 28 in pneumatic communication with the tube 13 leading to the patient for exhale purposes. Diaghragm 26, which is preferably made from very light elastomeric material, serves as a pilot-operated movable valve member connected in pneumatic communication with a patient's airway to control the instantaneous gaseous pressure within the lungs of the patient during ventilation. The Venturi port 25 of pilot valve 15 is operably connected to diaphragm 26 for adjustably moving the diaphragm as a function of the gaseous pressure at Venturi port 25. This gaseous pressure will always remain in balance with the pressure of the exhaled air from the patient, and will be a direct function of the instantaneous position of diaphragm 26 relative to the opening 28.

The exhaust port 24 of pilot valve 15 is formed exteriorly through manifold 22 and is centered about a reference axis shown at line X—X. A flow restrictor 30 is adjustably positioned in the exhaust port 24 of the pilot valve 15 for motion with a range of movement between first and second limits while centered along the reference axis X—X. An electromagnetic linear actuator 31 is also centered coaxially along the reference axis X—X. It is coupled to the flow restrictor 30 for selectively positioning the flow restrictor relative to the exhaust port 24 along the reference axis X—X. The electromagnetic linear actuator 31 includes a stationary permanent magnet 32 and an adjacent movable coil 33 wrapped about a supporting former 34 that mounts a needle valve element 35. Permanent magnet 32, coil 33, former 34 and needle valve element 35 are each coaxially centered along the reference axis X—X. Needle valve member 35 partially extends within a coaxial bore 36 defining the outer end of exhaust port 24.

An opening 41 through the manifold 22 leads to a conventional pressure transducer 18 that provides a measurement of gaseous pressure within the Venturi port 25. Transducer 18 is used in a feedback loop for the associated computer 17 to provide instantaneous readings for the respirator system.

FIG. 3 schematically illustrates the interior components of the delivery gas flow control valve 12 and its associated pilot valve 16. Since the pilot valve 16 is structurally identical to the pilot valve 15 described with respect to FIG. 2, repetition of the previous description will be omitted and identical reference numerals used in the drawings to denote those components described above.

Control valve 12 functions as an augmented gas flow regulator to supplement natural breathing patterns of the patient being ventilated. Valve 12 and pilot valve 16 are housed in a common manifold 43. The flow control valve 12 includes a movable diaphragm 42 having one side in pneumatic communication with tube 14, which is adapted to be connected to a patient's airway. Its remaining side is in proximal pneumatic communication with the Venturi port 24 of pilot valve 16. Diaphragm 42 is mechanically coupled to a movable valve element 44 interposed upstream from the diaphram 42 in the pneumatic path leading to the previously-described tube 14. This path essentially includes an inlet duct 47, a variable volume chamber 48 and an outlet duct 49. Valve element 44 variably obstructs an orifice extending through a valve seat 45 in the manifold 43 at the junction between inlet duct 47 and chamber 48. The movable valve element 44 is maintained in engagement against the flexible diaphragm 42 by a light biasing compression spring 46. The spring 46 acts on valve element 44 in opposition to the pneumatic forces supplied through operation of pilot valve 16.

Delivery gas flow is monitored by a flow transducer 20 connected to manifold 43 through two exterior ducts 52 and 53. Flow transducers 20 is of conventional design, and measures the pressure differential across screen 50 for conversion into gas flow and patient airway pressure readings. A pressure transducer 54 is also provided in conjunction with the pilot valve 16 for monitoring the instantaneous operation of pilot valve 16 through the previously-described duct 41.

FIG. 4 illustrates structural details of a prototype pilot valve that was constructed to verify the utility of the present valve structure. The pilot valve was modeled from an industrial Venturi tube identified as the MiniVac (MV-75-D) from Bay Pneumatics in Redwood, Calif. In contrast to the schematic showing of in-line Venturi tubes in FIGS. 2 and 3, the valve in FIG. 4 utilizes an angular gaseous path, where the incoming gas is deflected ninety degrees before passing across the Venturi openings. This general design was selected because the available Venturi tubes have the ability to produce a wide range of Venturi outlet pressures from negative to positive, depending upon the restriction encountered in the exhaust of the tube. The illustrated valve design lends itself readily to electromagnetic control by use of a linear motor or actuator, since a relatively minimal force is required to counteract the pneumatic forces encountered in the valve exhaust port 24.

The pilot valve shown at the top of FIG. 4 includes a custom-made manifold 55 having two perpendicular bores formed through it. The horizontal bore supports an axial inlet nozzle 56 arranged inwardly from the inlet port 23 and a coxial Venturi insert 57 that supports a central diverter 58. The diverter 58 has an interior cylindrical configuration that, together with the annular interior wall of the insert 57, defines the Venturi gap for the device. The larger outer end of diverter 58 has a square cross-sectional configuration and is press fit within the interior of the insert 57. The resulting gaps between the cylindrical and square surfaces of the connected insert 57 and diverter 58 serve as passages for flow of gas from the perpendicular Venturi openings surrounding diverter 58 to the Venturi port 25.

The interior of nozzle 56 and insert 57 are located within a perpendicular bored valve cavity 59 that intersects the horizontal cavity through the manifold 55. It is closed at one end by a solid threaded plug 60. Its opposite end is accurately machined to form the bore 36 at the exhaust port 24 of the valve.

In this experimental valve structure, the range of movement of needle valve 35 relative to manifold 55 between its limits of motion required for the full range of pilot pressures at Venturi port 25 was 0.10 inches along the reference axis X—X. Bore 36 had a diameter of 0.200 inches. The diameter of the cylindrical stem for needle valve element 35 was 0.002 inches less than the bore diameter. The active end of the needle valve element 35 was tapered at 5 degrees along 0.120 inches of its length, and its tip was spherically rounded. All surfaces of the needle valve element 35 were smoothed with 400 grit abrasive paper.

The electromagnetic linear actuator 31 used for controlling the position of needle valve element 35 relative to manifold 55 was constructed from components taken from a conventional loudspeaker of the type found in a small television speaker assembly. The permanent magnet 32 was anchored in stationary position relative to manifold 55, and supported a movable coil 33 and former 34 through the usual speaker bellows. However, the usual bellows were subsequently replaced by bowed springs 62 designed so that the full range of movement of needle valve element 3 could occur while the moving coil assembly "pushed" outwardly against the spring 62. This resulted in a more linear sequence of movement between needle valve 35 and the variable voltage applied to coil 33 and lower hystersis in comparison to that caused by friction of the typical fiber composite bellows used in loudspeakers. The linear rate of travel is acheived by utilizing a biasing spring attached to coil 33 which can be either a compression spring or a tension spring through its full range of movement. Electrical leads 61 were provided to the mounting ends of the leaf springs 62 for carrying current to the floating coil structure.

The prototype valve shown in FIG. 4 was used to operate a conventional exhale valve taken from a respirator breathing circuit. Control electrical wave forms were generated on the elecrical lead 61 by an electronic laboratory sine and square wave signal generator and coupled power amplifier. Sine waves from 0.1 to 50 Hz were used in testing the valve. Output pressure amplitude at Venturi port 25 was found to begin to attenuate at approximately 30 Hz. When applied to a patient ventilator, the pilot pressure at Venturi port 25 should be close coupled to directly actuate the patient circuit exhale valve in the manner schematically shown in FIG. 2, with pneumatic coupling designed for minimal compression volume. The diaphragm 26 should be molded from silicone rubber and be of minimal mass. These optimizing design parameters provide the exhale valve with sufficient responsiveness for High Frequency Ventilation pressure control.

Figure 6:
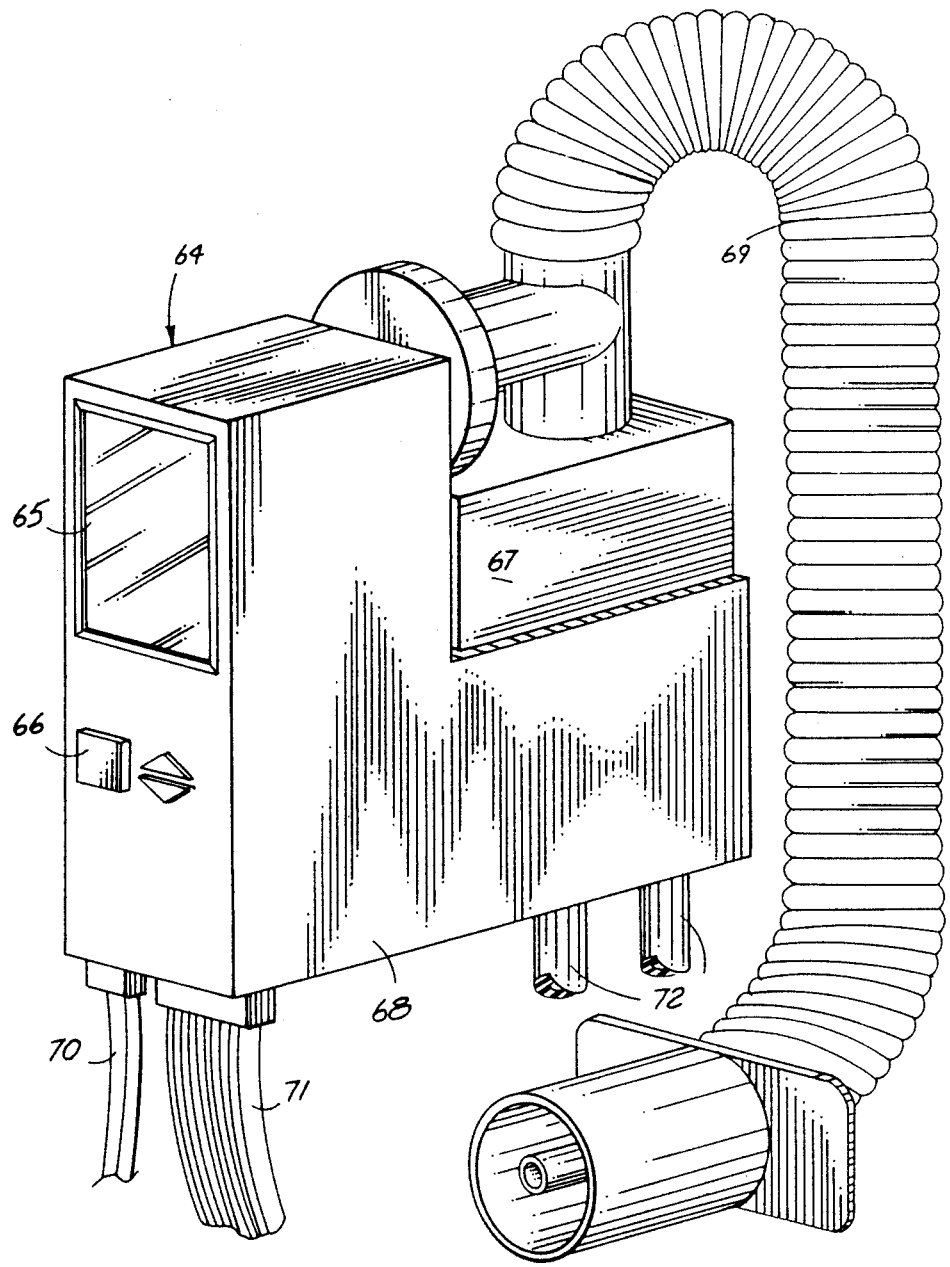
FIG. 6 is a perspective view of a patient interface module.

General physical and structural details of a respirator system designed according to this disclosure are illustrated in FIGS. 5, 6 and 7. The layout of such a system is shown in FIG. 5. It generally includes a gas supply 10 in which medical breathing gas (compressed air and oxygen) is supplied both in high pressure tanks (up to 2500 psi) and from conventional hospital pipe line walls outlets 40 to 60 psi). Both compressed air and oxygen from these sources must be reduced to a working pressure of approximately 30 psi and filtered to remove particulate and liquid contaminants before being delivered to the patient interface module 64. These functions can best be performed by large scale industrial components which can be housed in a separate chassis or within the bed system chassis for the patient.

An electrical power supply 63 includes a system that can interface with any external power source and can accommodate the wide range of voltages and frequencies found internationally, as well as vehicular power supplies that are encountered when using the system in ambulances and aircraft. The power supply 63 includes transformer, rectifying and filtering circuits required to regulate available electrical power supplies to the power input specifications of the patient interface module 64 and computer 17. Power supply 63 includes electrical batteries to provide a portable and back-up supply of electricity in case of the unavailablity or loss of the external power source.

The patient interface module 64, which is also illustrated in FIGS. 6 and 7, contains only those portions of the respirator system needed, by their intended functions, to be located directly adjacent to the patient to minimize the compression volume of the patient breathing circuit. It is designed separately from the gas supply 10, which is connected to it by conventional plumbing. It is also physically separate from the power supply 63, although versions of the patient in the face module can be designed for specific external power sources requiring only a connecting electrical cord. While the patient interface module 64 preferably includes an on-board dedicated microprocessor and programmable memory devices, these devices should be accessible through external ports, for programming purposes, by use of an external computer 51.

The patient interface module 64 essentially includes the basic system computer circuits, the computer to pressure interface valves, the oxygen/compressed air mixture control assembly and feedback sensors, the breathing gas flow control and pressure transducers, and a breathing gas conditioning assembly, plus a short length of patient breathing circuit conducting hose. The exterior of the module 64 (FIG. 6) includes a visual display screen 65 and a control keypad 66 arranged to face to the side of the patient. A breathing gas conditoning module 67 mounts in a recess in the top of the patient interface module chassis 68. The patient connector hose 69 might be a coaxial arrangement of the previously-described tubes 13 and 14. Hose 69 carries breathing gas from the conditioning module 67 to the patient and returns exhaled gas from the patient to the exhale gas pressure control valve 11. Electrical power cables 70 and computer interface cables 71 lead to the base of the chassis 68. Breathing gas is supplied from the separately-housed filter and pressure regulator components of the gas supply 10 through tubes 72.

FIG. 7 is a schematic elevation view showinng the interior components of the patient interface module 64. It includes an integrated pneumatic manifold 73 within which the supply gases received through hoses 72 are filtered, regulated and mixed. The incoming gases are directed from manifold 73 to the delivery gas flow control valve 12, where its output pressure and flow is measured by the previously-described transducers 54 and 18. The controlled flow of gas is then directed through the gas conditioning module 67 and exits through tube 14 to the patient.

Also included within the module 64 are the exhale gas pressure control valve 11 and the two computer-operated pilot valves 15 and 16, which were previously described in detail. A system control computer circuit board 74 is mounted below the pneumatic components of the module and has suitable connectors to external power, other computer systems, the pressure monitoring transducer circuitry, an oxygen concentration sensor circuit and the display/operator input circuits. Board 74 also includes motor control circuitry for the gas mixer, power conditioning circutiry for the computer circuits, and circuits for power amplification and conversion between digital and analog signals as required for the transducers included within the system.

OPERATION OF RESPIRATOR SYSTEM

When using the illustrated system for ventilating the lungs of a patient, the controlling electrical signals for pilot valves 15 and 16 are produced as a function of continuously cycled computer data files and computer control programs that will constantly monitor patient vital signs and operating parameters of the system to provide ventilation at pressures, temperatures, waveform shapes and flow rates matching the desired treatment. Digital data signals from the computer 17 are fed to a digital-to-analog converter to generate a stepped voltage waveform of the desired configuration as dictated by the controlling program. This waveform is then smoothed by electronic filtration and amplified to supply the coils 33 associated with the pilot valves 15 and 16. The electromotive forces on the formers 34, which will be a function of the voltages applied to the coils 33, will consantly balance against the loading of springs 62 and the force exerted by the flow of gas exiting from the exhaust ports 24 to position needle valve elemnts 35 within the bores 36. Due to the low venturi driving pressures, the low mass of the actuating coils 33 and associated needle valve elements 35, the light loading of springs 62 and substantially frictionless action in such moving coil transducers, an accurate high frequency response is achievable is achievable. The resulting instantaneous positions of the needle valve elements 35 constantly regulate the output pressure of the pilot valves 15 and 16 by impeding the flow of gas exiting through their respective exhaust ports 24.

The output pressures through the venturi ports 25 of the pilot valves 15 and 16 are constantly measured by the monitoring pressure transducers 18 and 54, respectively. The pressure signals, after being digitized, are fed back to the control program, along with gas flow data from transducer 20, in a feedback loop to permit regulation of the system on a real-time basis. Based upon the control algorithm the computer control data file can be successively updated to bring the system functions closer to a predetermined optimum. In this manner the physical behavior of the various valve components described above can be automatically adapted, through software commands, to meet the operator's and the patient's requirements. By controlling the pilot valves 15 and 16 by computer-generated signals, more precise control of gas flow rate-vs-time waveform configurations, the phase angle of the flow rate waveform relative to the pressure waveform, and limitation of pressure spikes can be achieved.

An additional feature of the delivery gas flow control valve 12 is its function as a "demand regulator" for the patient's spontaneous breathing efforts. As the patient begins to breath inwardly, the ventilator breathing circuit pressure in the variable volume chamber 48 of manifold 43 (FIG. 3) will drop slightly. This reduction in pressure unbalances diaphragm 42, causing it to open the supply valve element 44 slightly until equilibrium is again achieved. Particularly when applied to small premature infants, who are weak and often of very compromised physical condition, only slight efforts for spontaneous breathing are to be allowed, thus conserving their energy. Mechanical demand valves, such as are used in certain prior ventilating systems intended for use with adult patients, require significant mechanical forces to operate. A portion of the control program for computer 17 must address the need to mechanically enhance the response characteristics of the control valve 12 in response to specified and characteristic variations in the continuously monitored breathing circuit pressure. The ability to constantly monitor and accurately respond to pressure variations under computer contol can be used to limit the patient effort required to operate, and the response characteristics of, the flow regulator embodied in control valve 12 when utilized as a breathing "demand" valve for high risk patients. Due to the excellent responsiveness of the linear actuators 31, precise control of both breathing circuit pressure and flow rate are possible at cycling rates and waveform configurations up to the upper limits of known medical utility. The electromagnetic linear actuators 31 have no obligate step sequence and can be driven from one end of the range of motion of needle valve 35 to the other in a single step. The linear actuator 31 is adaptable to the maximum number of control signal voltage level steps available at the output of the selected system control computer 17 had the interfacing digital-to-analog converter circuitry. Over 1,000 steps are inexpensively achievable with presently available integrated circuit technology. The linear actuators 31 have a relatively low physical inertia. They are available or can be constructed form available components having the high-fidelity response rates required for precise waveform generation, including High Frequency Ventilation. Critical dampening of the action of control valve 11 to prevent pressure spikes in the patient circuit and enhanced "demand valve" action in the operation of control valve 12 are within reach of the control system to a much improved degree over the ventilators currently available In compliance with the statute, the invention has been described in language more or less specific as to structural features. It is to be understood, however, that the invention is not limited to the specific features shown, since the means and construction herein disclosed comprise a preferred form of putting the invention into effect. The invention is, therefore, claimed in any of its forms or modifications within the proper scope of the appended claims, appropriately interpreted in accordance with the doctrine of equivalents.

I claim:

1. A respirator system capable of ventilating the lungs of a patient by providing cycle rate, pressure and flow wave form requirements needed over a full range of operational control from Continuous Positive Airway Pressure, through Intermittent Mandatory Ventilation, to High Frequency Ventilation, comprising:

a control valve including a control port leading to a pilot-operated movable valve member interposed between two pneumatic ports, one of which is adapted to be in communication with a patient's airway;

a pilot valve having an inlet port, an exhaust port, and a Venturi port, the inlet and exhaust ports of the pilot valve being directed across a region of gaseous flow intersected perpendicularly by an opening leading to the Venturi port;

the Venturi port of the pilot valve being operably connected to the control port of the movable valve member of the control valve for adjustably shifting the movable valve member as a function of the gaseous pressure at the Venturi port;

the exahust port being centered about a reference axis;

flow restrictor means adjustably positioned in the exhaust port of the pilot valve for motion within a range of movement between first and second limits while centered along the reference axis;

electromagnetic linear actuator means centered coaxially along the reference axis and coupled to the flow restrictor means for selectively shifting the positioning of the flow restrictor means relative to the exhaust port along the reference axis; and electronic processing means operably connected to the electromagnetic linear actuator means for generating electrical signals as a function of a stored computer program, the electrical signals being directed to the electromagnetic linear actuator means for selecting the instantaneous position of the flow restrictor relative to the exhaust port along the reference axis;

the electromagnetic linear actuator means comprising:

a stationary loudspeaker permanent magnet centered coaxially along the reference axis;

a moving loudspeaker electromagnetic coil member centered coaxially along the reference axis adjacent to the permanent magnet, the flow restrictor means being mounted to the coil member for conjoint movement with it relative to the permanent magnet along the reference axis; and spring means yieldably connected to the coil member for biasing it parallel to the reference axis in opposition to forces imparted to the coil member by the adjacent permanent magnet.

2. The respirator system of claim 1 wherein the control valve is a diaphragm-operated exhale pressure relief valve in which the remaining pneumatic port is exhausted to atmosphere.

3. The respirator system of claim 1 wherein the control valve is a diaphragm-operated exhale valve in which the remaining pneumatic port is exhausted to atmosphere; and
pressure monitoring means operably connected to the Venturi port of the pilot valve;
the pressure monitoring means being operably connected to the electronic processing means in a feedback loop.

4. The respirator system of claim 1 wherein the fluid control valve is a diaphragm-operated delivery flow control valve in which the remaining pneumatic port is adapted to be connected to a pressurized gas supply.

5. The respirator system of claim 1 wherein the control valve is a diaphragm-operated delivery flow valve in which the remaining pneumatic port is adapted to be connected to a pressurized gas supply, the control valve having one side of a movable diaphragm in pneumatic communication with a tube serving as the one control valve port adapted to lead to a patient's airway, its remaining side being in pneumatic communication wth the Venturi port of the pilot valve.

6. The respirator system of claim 1 wherein the fluid control valve is a diaphragm-operated delivery flow valve in which the remaining pneumatic port is adapted to be connected to a pressurized gas supply, the control valve having one side of a movable diaphragm in pneumatic communication with a tube serving as the one control valve port adapted to lead to a patient's airway, its remaining side being in pneumatic communication with the Venturi port of the pilot valve, the diaphragm being mechanically coupled to a movable valve element interposed upstream from the diaphragm in the pneumatic path leading to the tube.

7. The respirator system of claim 1 wherein the fluid control valve is a diaphragm-operated delivery flow valve in which the remaining pneumatic port is adapted to be connected to a pressurized gas supply; and
flow monitoring means operably connected to the tube at a location between the valve element and the patient for measuring instantaneous gaseous flow within the tube;
the flow monitoring means being operably connected to the electronic processing means in a feedback loop.

8. The respirator system of claim 1 wherein the fluid control valve is a delivery flow valve in which the remaining port is adapted to be connected to a pressurized gas supply; and
pressure monitoring means operably connected to the Venturi port of the pilot valve for measuring instantaneous pressure within the tube;
the pressure monitoring means being operably connected to the electronic processing means in a feedback loop.

9. The rirator system of claim 1 wherein the spring means is shaped to act as either a compression or tension spring throughout the range of movement of the flow restrictor along the reference axis.

10. The respirator system of claim 1 wherein the exhaust port of the pilot valve includes a subsantially cylindrical outer bore;
the flow restrictor means comprising a tapered needle valve element movably centered within the bore along the reference axis.

11. A respirator system capable of ventilating the lungs of a patient by providing cycle rate, pressure and flow wave form requirements needed over a full range of operational control from Continuous Positive Airway Pressure, through Intermittent Mandatory Ventilation, to High Frequency Ventilation, comprising: comprising:
an exhale gas pressure control valve, including a control port leading to a pilot-operated movable valve member interposed between two pneumatic ports;
a first tube leading from one pneumatic port of the exhale gas pressure control valve and adapted to be connected in pneumatic communication with a patient's airway, the remaining pneumatic port of the exhale gas pressure control valve being exhausted to atmosphere;
a delivery gas flow control valve, including a control port leading to a pilot-operated movable valve member interposed between two pneumatic ports;;
a gas conduit adapted to interconnect the one pneumatic port of the delivery gas flow control valve to a source of pressurized gas, the remaining pneumatic port of the delivery gas flow control valve being connected to a second tube adapted to be connected in pneumatic communication with a patient's airway;
first and second pilot valves respectively connected to the control ports of the two control valves, each pilot valve having an inlet port, an exhaust port, and a Venturi port, the inlet and exhaust ports of each pilot valve being directed across a region of a gaseous flow that is intersected perpendicularly by an opening leading to its Venturi port;
the Venturi ports of the pilot valves being operably connected to the pilot operated movable valve members of the respective control valves for adjustably shifting the valve members as a function of the fluid pressures at the Venturi ports;
the exhaust ports of the pilot valves being centered about separate reference axes;
individual flow restrictor means adjustably positioned in the respective exhaust ports of the pilot valves for motion within a range of movement between first and second limits along the reference axes;
separate electromagnetic linear actuator means positioned coaxially along the reference axes and coupled to the respective flow restrictor means of each pilot valve for selectively positioning the flow restrictor means along its reference axis between its first and second limits; and
electronic processing means operably connected to the electromagnetic linear actuator means for generating electrical signals as a function of a stored computer program and for directing the generated electrical signals to the electromagnetic actuator means of the first and second pilot valves for selecting the instantaneous positions of their respective flow restrictor means relative to the exhaust ports of the two pilot valves along the reference axes;
the electromagnetic linear actuator means for each control valve comprising:
a stationary loudspeaker permanent magnet centered coaxially along the reference axis;

a moving loudspeaker electromagnetic coil member centered coaxially along the reference axis adjacent to the permanent magnet, the flow restrictor means being mounted to the coil member for conjoint movement with the coil member relative to the permanent magnet along the reference axis; and spring means yieldably connected to the coil member for biasing the coil member along the reference axis in opposition to forces imparted to the coil member by the adjacent permanent magnet.

12. The respirator system of claim 15 further comprising gas pressure monitoring means operably connected to the first tube for measuring insantaneous gaseous pressure within the first tube;

the gas pressure monitoring means being operably connected to the electronic processing means in a feedback loop.

13. The respirator system of claim 15 further comprising:

gas flow monitoring means operably connected to the second tube for measuring instantaneous gaseous flow within the second tube;

the gas flow monitoring means being operably connected to the electronic processing means in a feedback loop.

14. The respirator system of claim 15 wherein:

the exterior of the exhaust port of each pilot valve includes a substantially cylindrical outer bore centered along the reference axis; and the flow restrictor means for each of the flow control valves comprises a tapered needle valve element movably centered with the bore along the reference axis.

15. The respirator system of claim 11 wherein the spring means of each pilot valve is shaped to act as either a compression or tension spring throughout the range of movement of its flow restrictor along the reference axis.

16. A pilot valve for use in a patient respirator system capable of ventilating the lungs of a patient by providing respirator system capable of ventilating the lungs of a patient by providing cycle rate, pressure and flow wave form requirements needed over a full range of operational control from Continuous Positive Ariway Pressure, through Intermittent Mandatory Ventilation, to High Frequency Ventilation, comprising:

a manifold having a gas inlet port, a gas exhaust port, and a Venturi port, the gas inlet port being adapted to be operably connected to a source of pressurized gas and the Venturi port being adapted to be operably connected to the control port of a pilot-controlled respirator control valve;

the gas inlet and exhaust ports being directed within the manifold across a region of gaseous flow that is intersected perpendicularly by an opening leading to the Venturi port;

the exhaust port being centered about a reference axis;

flow restrictor means movably located within the gas exhaust port of the manifold for motion within a range of movement between first and second limits while centered along the reference axis; and electromagnetic linear actuator means centered coaxially along the reference axis and coupled to the flow restrictor means for selectively positioning the flow restrictor means relative to the exhaust along the reference axis between its first and second limits, the electromagnetic linear actuator means comprising:

a stationary loudspeaker permanent magnet centered coaxially along the reference axis;

a spring-loaded and electrically conductive loudspeaker coil coaxially centered along the reference axis for movement relative to the permanent magnet without frictional contact between them, such that delivery of electrical signals to the coil will cause it to be located along the reference axis at a predictable instantaneous axial position, the flow restrictor means being mounted to the coil member for conjoint movement with it relative to the permanent magnet along the reference axis.

17. The pilot valve of claim 16 wherein:

the exterior of the exhaust port of the manifold includes a substantially cylindrical outer bore centered along the reference axis; and the flow restrictor means comprises a tapered needle valve movably centered within the bore along the reference axis.

18. The pilot valve of claim 16 wherein:

the exterior of the exhaust port of the manifold includes a substantially cylindrical outer bore centered along the reference axis; and the flow restrictor means comprises a tapered needle valve movably centered within the bore along the reference axis;

the electromagnetic linear actuator means comprises:

a stationary permanent magnet centered coaxially along its reference axis;

a moving electromagnetic coil member centered coaxially along its reference axis adjacent to the permanent magnet, the flow restrictor means being mounted to the coil member for conjoint movement with the coil member relative to the permanent magnet along its reference axis; and spring means yieldably connected to the coil member for biasing the coil member along its reference axis in opposition to forces imparted to the coil member by the adjacent permanent magnet.

* * * * *